United States Patent [19]
Hennessy et al.

[11] Patent Number: 5,840,324
[45] Date of Patent: Nov. 24, 1998

[54] ANTIPARASITIC COMPOSITIONS

[75] Inventors: Desmond Ronald Hennessy, North Epping; John Richard Ashes, Wahroonga; Trevor William Scott, Kellyville; Suresh Kumar Gulati, Eastwood; John Winston Steel, Castlecrag, all of Australia

[73] Assignee: Commonwealth Scientific and Industrial Organisation, Parkville, Australia

[21] Appl. No.: 549,755

[22] PCT Filed: May 24, 1994

[86] PCT No.: PCT/AU94/00272

§ 371 Date: Mar. 13, 1996

§ 102(e) Date: Mar. 13, 1996

[87] PCT Pub. No.: WO94/27598

PCT Pub. Date: Dec. 8, 1994

[30] Foreign Application Priority Data

May 26, 1993 [AU] Australia ................. PL9030

[51] Int. Cl.[6] ................. A61K 9/14; A61K 9/52
[52] U.S. Cl. ................. 424/418; 424/439; 424/438; 424/442; 424/499
[58] Field of Search ................. 424/439, 438, 424/442, 499, 418

[56] References Cited

U.S. PATENT DOCUMENTS

| | | |
|---|---|---|
| 4,547,491 | 10/1985 | Mrozik et al. . |
| 4,587,247 | 5/1986 | Linn et al. . |
| 5,190,775 | 3/1993 | Klose . |
| 5,252,561 | 10/1993 | Hornykiesytsch . |

FOREIGN PATENT DOCUMENTS

| | | |
|---|---|---|
| 402712 | 6/1966 | Australia . |
| 23456/70 | 12/1969 | Australia . |
| 450530 | 12/1969 | Australia . |
| 66259/81 | 1/1980 | Australia . |
| 10311/83 | 1/1982 | Australia . |
| 17927/83 | 8/1982 | Australia . |
| 69739/87 | 3/1987 | Australia . |
| 0 074 758 A1 | 3/1983 | European Pat. Off. . |
| 0 125 004 A1 | 11/1984 | European Pat. Off. . |
| 0288205 A2 | 10/1988 | European Pat. Off. . |
| 0447100A1 | 9/1991 | European Pat. Off. . |
| 0 465 121 A1 | 1/1992 | European Pat. Off. . |
| 0497240A1 | 8/1992 | European Pat. Off. . |
| 2 094 625 | 3/1982 | United Kingdom . |
| 91/08669 | 6/1991 | WIPO . |
| 92/08454 | 5/1992 | WIPO . |

OTHER PUBLICATIONS

Hennessy et al at the Joint Conference of the New Zealand and Australian Societes for Parasitology, Auckland, New Zealand, 1992.

Hennessy et al, "The Disposition of Albendazole in Sheep", *J. vet Pharmacol. Therap.*, 12, 1989, pp. 421–429.

*Primary Examiner*—Jeffrey C. Mullis
*Attorney, Agent, or Firm*—Lowe Hauptman Gopstein Gilman & Berner

[57] ABSTRACT

This invention concerns the delivery of anti-parasitic agents to ruminant animals. More particularly, the invention concerns delivery of such agents in a controlled manner to enable the agent to have maximum effect on the parasite for longer times than is possible with conventional formulations. The composition of the invention comprises a benzimidazole, macrocyclic lactone, organophosphate, salicylanilide/substituted phenol, tetramisole or pyrimidine anti-parasitic agent dispersed in a medium the solubility characteristics of which are such as to ensure that, following oral administration, controlled amounts of the anti-parasitic agent become available to the parasite, either directly or by absorption into the ruminant blood plasma, during passage of the composition through the rumen, the abomasum and the intestine.

24 Claims, 11 Drawing Sheets

ANTIPARASITIC COMPOSITIONS

TECHNICAL FIELD

This invention concerns the delivery of anti-parasitic agents to ruminant animals. More particularly, the invention concerns delivery of such agents in a controlled manner to enable the agent to have maximum effect on the parasite for longer times than is possible with conventional formulations.

BACKGROUND ART

Anti-parasitic agents are frequently delivered to ruminants in the form of oral drenches directly into the rumen. Because of chemical and bacterial degradation, association with digesta, uncontrolled absorption and excretion, the dosages required for useful effect will generally need to be considerably in excess of what might be anticipated from observation of in vitro exposure of a parasite to a given anti-parasitic agent. The elevated dosages are undesirable not only from the direct cost point of View, but also because of the contribution to the accumulation of is chemical residues (i) in edible tissues and, (ii) in the environment as they are excreted from the animal.

The present invention avoids the aforementioned disadvantages associated with prior art anti-parasitic agent administration, in that it permits greater anti-parasitic action to be achieved with existing dosages, or allows existing rates of parasite control to be maintained with lower dosage rates. The invention is based on the discovery of a novel concept of staged delivery of anti-parasitic agent to three sites, the rumen, the abomasum and the small intestine.

An important function of the rumen is to break down materials ingested by the animal in order to facilitate their absorption and utilisation. There are some nutrients from which better economic benefits would be derived if they were to pass unchanged through the rumen to become available for absorption from the abomasum or the small intestine. For example, it has been known for many years that the amino acid methionine is substantially degraded in the rumen, and that the introduction of methionine directly into the abomasum can lead to enhanced wool growth. Ferguson et al. (1969)[1] and Scott et al (1972)[2] describe chemical carriers or coatings designed to provide feedstuffs, including amino acids, with substantially 100% protection from rumen degradation so as to enhance ruminant productive capacity. Those disclosures were specifically directed to nutritional improvement. They did, however, allude to the possibility of the various protectants having value for transporting therapeutic and prophylactic agents. Evidence that this might be so was provided by work reported by Hennessy et al[3], which indicated that oral administration of albendazole (ABZ) protected from rumen degradation by encapsulation in a simple formaldehyde-treated lipid/protein matrix resulted in an increased concentration of ABZ in abomasal fluid compared with that following oral dosage with a conventional formulation from which the ABZ was freely presented to the rumen. While such prior art is acknowledged as a precursor of the present invention, the present invention is distinguished by its use of the surprising finding that the efficacy of anti-parasitic agents can be dramatically improved by administering them in a form which specifically and proportionally divides the dose and ensures a controlled degree of availability at various sites in the gastrointestinal tract, including the rumen, abomasum and small intestine.

Conventionally (oral) administered benzimidazole anthelmintic compounds are rapidly absorbed, predominantly from the rumen, and are extensively metabolised (with concomitant reduction in metabolite potency) before excretion in urine and bile. This behaviour significantly limits the availability of active metabolites at the sites of parasite infection—namely the lumen of the abomasum and small intestine.

Absorption of macrocyclic lactones from the rumen initiates similar metabolism. In addition, some chemical degradation of the active occurs within the rumen as well as extensive (and strong association of active with rumen digesta material. This association also significantly limits availability and it is suggested that it contributes to the large portion of the dose which is transported through the gastrointestinal tract, potentially unavailable for contact with the parasite. Large quantities of active parent drug are then excreted in faeces and it is these contaminants in faeces that are considered to deleteriously impact on fauna beneficial in pasture degradation of the faecal material. Organophosphates function by inhibiting enzymes, particularly acetyl choline esterase in the parasite and host. The compounds are rapidly absorbed from the rumen which causes a corresponding rapid depression of enzyme activity in the host, in many cases this is lethal. Organophosphates therefore have a very low safety index. Reducing the rapid absorption of organophosphates from the rumen and extending or directing their availability to parasites in the abomasum and intestine is advantageous in that toxicity to the host would be reduced while maintaining antiparasitic activity.

Salicylanilides such as closantel very strongly associate with plasma albumin. This action retains the drug in the bloodstream at levels that are efficacious against blood-consuming parasites for prolonged periods (about 3–4 weeks), providing an obvious prophylactic effect. Closantel is, however, slowly absorbed and about 50% of the dose is lost in faeces as the dose bolus is naturally transported in digesta past the site(s) of absorption in the gastrointestinal tract. Controlling the dose by broader presentation at the rumen, abomasum and intestine can increase quantitative absorption and by definition of the pharmacokinetic behaviour of closantel, the residence time and therefore protective period can be extended.

Levamisole and the morantel/pyrantel chemical class of antiparasitic agents are rapidly absorbed from the rumen, the maximum concentrations in the bloodstream occurring within 2–4 hours of oral administration. They are rapidly metabolised, in the case of morantel/pyrantel the absorbed compound is degraded at a rate consistent with first-pass metabolism; the products then being completely inactive. Absorption and metabolism can be so extensive that insufficient dose is even available to affect parasites at distal sites of the intestine, this being of significant importance since only drug which is retained in the gut is active. Absorbed drug is rapidly excreted, predominantly in urine. By reducing absorption from the rumen and directing large portions of the dose to the abomasum and intestine a greater availability of active drug to the parasite in the gut lumen is obtained.

While some absorption of drug from the rumen can define the initial availability of drug as this portion recycles between the bloodstream and gastrointestinal tract before clearance, it is crucial that absorption from the rumen be controlled and restricted to minimise loss of active from the gut environment. The absorption from the rumen, or degradation/association with rumen digesta severely limits the availability of a highly active parent compound at the site of parasite habitation, in the lumen of the abomasum and small intestine.

Traditionally, increased anthelmintic action (particularly against drench resistant parasites) necessitated the administration of multiple dose rates. This is costly and in some cases lethal to the host animal. Furthermore, the value of increased dose is limited since the dose is cleared following first-order kinetics, that is, the clearance is directly related to the quantity of drug present. The high concentrations that appear in the bloodstream after rapid and extensive absorption from the rumen are not available to the parasite for significantly longer duration than that achieved following a single dose. Because it is the duration of availability of an antiparasitic agent at the site of infection that is critical for activity the rapidly cleared, albeit initially high, concentrations are of little additional value.

By restricting absorption from the rumen and controlling the quantity of a single dose which is presented to the lumen of the abomasum and small intestine, similar increased activity against resistant parasites is achieved with the staged delivery of a single dose compared with the more expensive administration of multiple dose rates.

DISCLOSURE OF THE INVENTION

In its broadest aspect this invention provides a particulate composition for combating and preventing parasite infestation of ruminants, which composition comprises a benzimidazole, macrocyclic lactone, organophosphate, salicylanilide/substituted phenol, tetramisole or pyrimidine anti-parasitic agent dispersed in a medium the solubility characteristics of which are such as to ensure that, following oral administration, controlled amounts of the anti-parasitic agent become available to the parasite, either directly or by absorption into the ruminant blood plasma, during passage of the composition through the rumen, the abomasum and the intestine.

The benzimidazole antiparasitic agents include 2-(4-thiazolyl)-1H-benzimidazole, known as thiabendazole: [5-(propylthio)-1H-benzimidazol-2-yl]carbamic acid methyl ester, known as albendazole, [5-(propylsulfinyl)-1H-benzimidazol-2-yl]carbamic acid methyl ester known as albendazole sulfoxide or albendazole oxide: [2-(4-thiazolyl) -1H-benzimidazol-5-yl]carbamic acid 1-methylethyl ester, known as cambendazole: [5-(phenylthio)-1H-benzimidazol-2-yl]carbamic acid methyl ester, known as fenbendazole; (5-benzoyl-1H-benzimidazol-2-yl)carbamic acid methyl ester, known as fenbendazole; [5-(phenylsulfinyl)-1H-benzimidazol-2-yl]carbamic acid methyl ester, known as is oxibendazole, (5-propoxy-1H-benzimidazol-2-yl)carbamic acid methyl ester, known as oxibendazole, [5-(n-butyl)-1H-benzimidazol-2-yl]carbamic acid methyl ester known as parbendazole, methyl 5-cyclopropylcarbonyl-1H-benzimidazol-2-ylcarbamate known as ciclobendazole, methyl 5-(4-fluorobenzoyl)-1H-benzimidazol-2-ylcarbamate known as flubendazole, 5-chloro-6-(2,3-dichlorophenoxy)-2-(methylthio)-benzimidazole known as triclabendazole and [5-(4-fluoro-phenylsulfonyloxy)-1H-benzimidazol-2-yl]carbamic acid methyl ester known as luxabendazole.

The benzimidazole antiparasitic agents are active against Haemonchus, Osteragia, Trichostrogylusi, Nematodirus, Cooperia, Bunostomum, Strongyloides, Trichuris, Oesophagostomum, Chabertia, Dicryocaulus, Moniezia and Fasciola in sheep. They are active against Haemonchus, Ostertagia, Trichostrongylus, Nematodirus, Cooperia, Bunostomum, Capillaria, Strongyloides,Trichuris, Oesophagostomum, Chabertia, Dictyocaulus, Moniezia and Fasciola in cattle.

The macrocyclic lactone antiparasitic agent may be an avermectin or milbemycin, such as abamectin, ivermectin, doramectin or moxidectin, The macrocyclic lactone antiparasitic agents are active against Haemonchus. Ostertagia, Trichostronigylus, Nemarodirus, Cooperia, Strongyloides, Trichuris, Oesophagostomum, Chabertia and Dicryocaulus in sheep. They are active against Haemonchus, Ostertagia, Trichostrongylus, Nematodirus, Cooperia, Oesophagostomum and Dicryocaulus in cattle.

Organophosphate antiparasitic agents include bis(2-chloroethyl)-3-chloro-4-methylcoumarin-7-yl phosphate known as haloxon, tetraethyl-{(2-methoxy-p-phenylene)-bis-[imino(thiocarbonyl)]}diphosphoramidate known as imcarbophos, diethyl naphthylimido-oxyphosphonate known as naphthalophos.

The organophosphate antiparasitic agents are active against Haemonchus, Trichostrongylus, Cooperia, Oesophagostomum and Dicryocaulus in sheep. They are active against Haemonchus, Ostertagia, Trichostrongylus, Cooperia, Bunostomum and Oesophagostomum in cattle.

Salicylanilide/substituted phenol antiparasitic agents include 5'-chloro-4'-(4-chloro-α-cyanobenzyl)-3,5-diiodosalicyl-o-toluidide known as closantel, 2'-[2,3-bis-(methoxycarbonyl)guanidino]-5'-phenylthio-2-methoxyacetanilide known as febantel, 3,3',5,5',6-pentachloro-2'-hydroxysalicylanilide known as oxyclozanide, 3'-chloro-4'-(4-chlorophenoxy)-3,5-diiodosalicylanilide known as rafoxanide, 2',5-dichloro-4'-nitrosalicylanilide known as niclosamide, 4-cyano-2-iodo-6-nitrophenol known as nitroxynil. In vivo, febantel is metabolised to fenbendazole.

The salicylanilide/substituted phenol antiparasitic agents are active against Haemonchus and Fasciola in sheep. They are active against Haemonchus, Bunostomum, Oesophagostomum, Moniezia, Fasciola and Paramphistomum in cattle.

Tetramisole antiparasitic agents include (–)-(S)-2,3,5,6-tetrahydro-6-phenylimidazo[2,1-b]thiazole hydrochloride known as levamisole.

The tetramisole antiparasitic agents are active against Haemonchus, Ostertagia, Trichostrongylus, Nematodirus, Cooperia, Bunostomum, Strongyloides, Trichuris Oesophagostomum, Chabertia and Dictyocaulus in sheep. They are active against Haemonchus, Ostertagia, Trichostrongylus, Nematodirus, Cooperia, Bunostomum, Oesophagostomum, Chabertia, Dictyocaulus and Thelazia in cattle.

Pyrimidine antiparasitic agents include 1,4,5,6-tetrahydro-1-methyl-2-[(E)-2-(2-thienyl)-vinyl]-pyrimidine-4,4'-methylenebis-(3-hydroxy-2-naphthoate) known as pyrantel, (E)- 1,4,5,6-tetrahydro- 1 -methyl-2-[2-(3-methyl-2-thienyl)vinyl]-pyrimidine known as morantel, (E)-3-[2-(1,4,5,6-tetrahydro-1-methylpyrimidin-2-yl)vinyl] phenol-4,4-methylenebis-(3-hydroxy-2-naphthoate) known as oxantel, and salts of any, including citrate, tartrate and pamoate(embonate).

The pyrimidine antiparasitic agents are active against Haemonchus, Ostertagia, Trichostrongylus, Nematodirus, Cooperia, Trichuris, Oesophagostomum and Chabertia in sheep. They are active against Haemonchus, Ostertagia, Trichostrongylus, Nematodirus, Cooperia, Oesophagostomum and Chabertia in cattle.

In a preferred embodiment of this invention the anti-parasitic agent is dispersed in a protein/lipid medium possessing solubility characteristics selected to ensure the release of amounts of the active agent at sites in the intestinal tract. Preferred media are based on modified proteins, for example, proteinaceous substances such as plant or animal meals, casein and gelatin, which have been treated with cross-linking agents, eg. aldehydes, tannins, polyvalent cations and the like, or otherwise modified (eg. by heating) to acquire solubility characteristics offering preselected degrees of resistance to the various encountered in the ruminant gastrointestinal tract.

Accordingly, another aspect of this invention is a composition for combating and preventing parasite infestation of ruminants which comprises a benzimidazole, macrocyclic lactone, organophosphate, salicylanilide/substituted phenol, tetramisole or pyrimidine anti-parasitic agent dispersed in a proteinaceous matrix which undergoes staged degradation allowing controlled release of the anti-parasitic agent in each of the rumen, abomasum and intestine.

The degradation of proteinaceous media such as referred to above will occur firstly in the rumen through the activity of the microbial population, next in the abomasum where the more acidic conditions further solubilise the matrix, and finally in the small intestine due to enzymatic breakdown of proteins and fats.

In the case of lipid/protein matrices wherein the protein has been cross-linked by treatment with an aldehyde, we have found it possible, by varying the is proportions of ingredients and the degree of cross-linking, to provide formulations which will degrade at selected gastrointestinal sites in a predetermined way. This means that formulations can be tailored so that the active ingredient is released according to the pattern felt to be most conducive to its efficacy.

When the anti-parasitic agent is a benzimidazole, compositions according to this invention should ensure that the relative proportions of anti-parasitic agent which become available in the rumen, the abomasum and the small intestine are of the order of 1:4:5 respectively. For macrocyclic lactones the conventional availability is about 1:0.1:20 respectively, whereas rumen, abomasum and small intestine availabilities of 1:2:30 are likely to be more suitable. Appropriate availabilities for other classes of agents may be determined by routine experimentation.

BEST MODE OR MODES FOR CARRYING OUT THE INVENTION

Figure 1:
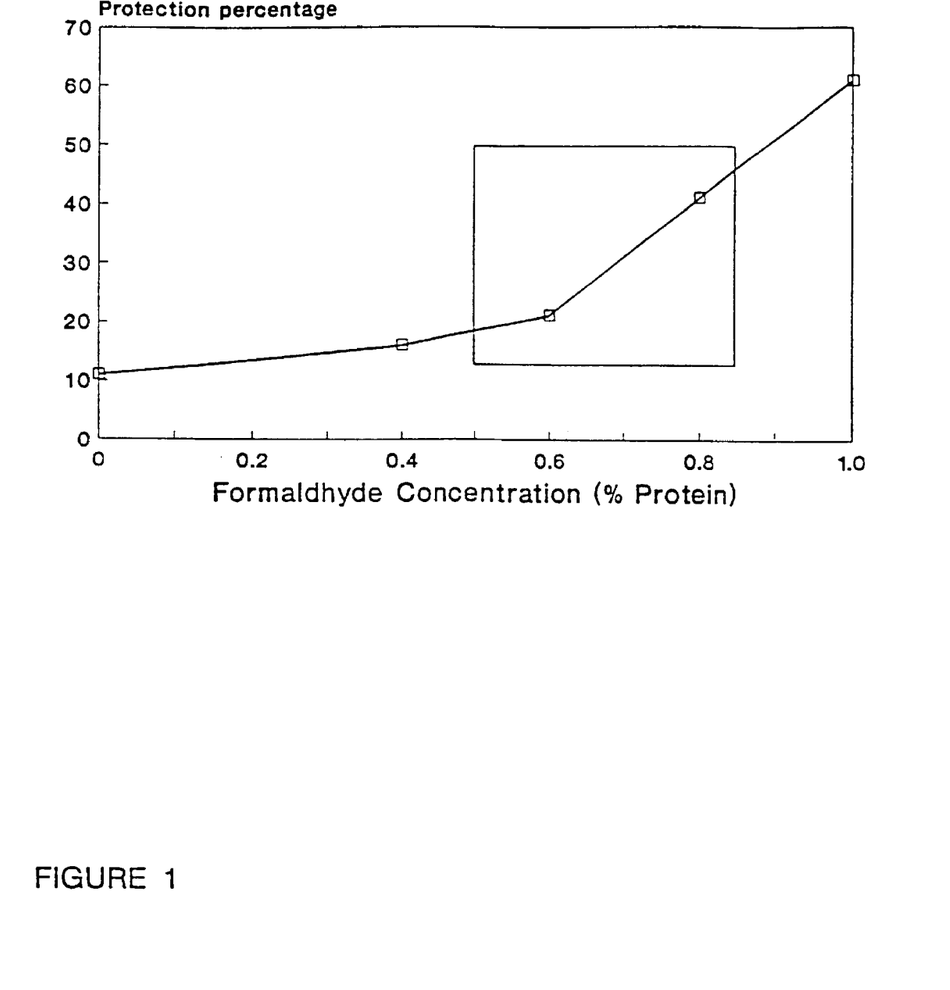
FIG. 1 illustrates the levels of formaldehyde treatment to achieve various degrees of protection.
Figure 2:
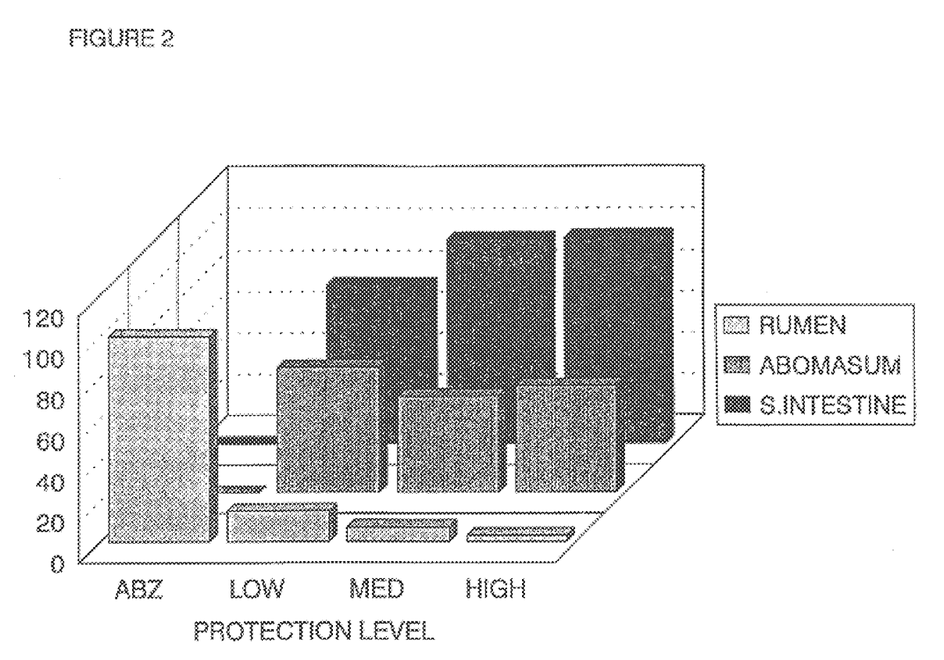
FIGS. 2 and 3 illustrate the release of benzimidazoles and macrocyclic lactones from variously protected protein matrices when incubated in fluid from the rumen, abomasum and small intestine under simulated in vivo conditions.
Figure 3:
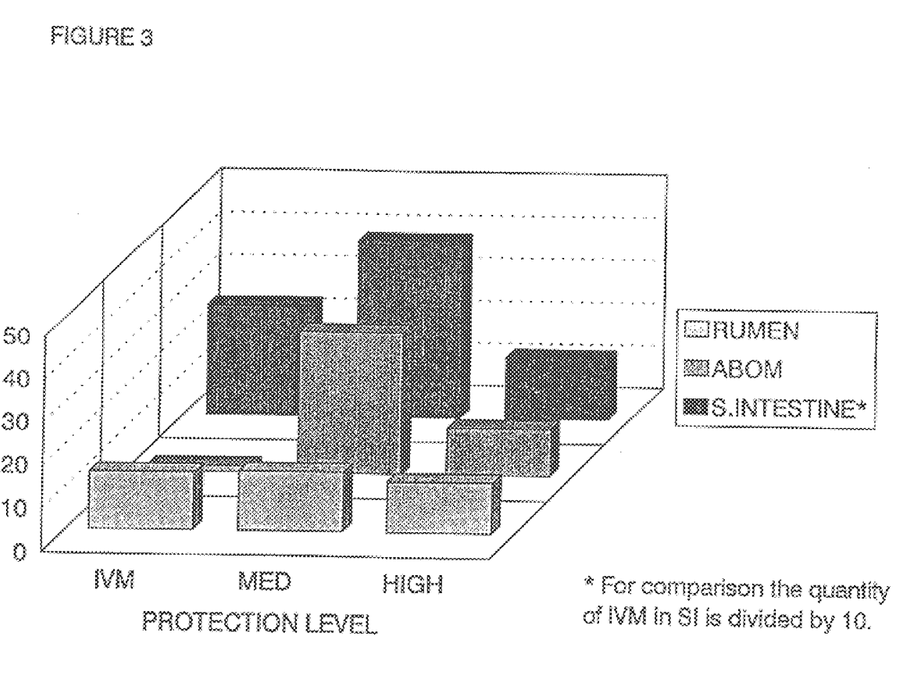

FIG. 1 illustrates the levels of formaldehyde treatment required to achieve various degrees of protection. FIGS. 2 and 3 illustrate the release of benzimidazoles and macrocyclic lactones from variously protected protein/lipid matrices when incubated in fluid from the rumen, abomasum and small intestine under simulated in vivo conditions. By reference to these figures the man skilled in the art should have no difficulty in designing formulations which will significantly enhance the efficacy of such agents. By routine experimentation it should be possible to design formulations for the delivery of other classes of anti-parasitic agents. Trials undertaken with sheep and cattle indicate that benzimidazole anthelmintic preparations according to this invention will increase the availability of the agent to a degree which leads to the elimination of up to 30% more benzimidazole-resistant worms than is achieved by the same dosage of a conventional benzimidazole preparation.

The invention will now be described in greater detail with reference to the following examples:

EXAMPLE 1

Preparation of 3-stage release anti-parasitic formulation (a) Benzimidazole.

40 g g ABZ were evenly dispersed in 20 mL vegetable oil, and the mixture was emulsified with 14% casein solution at pH 9. The emulsion was then freeze-dried and comminuted to form finely dispersed particles containing ABZ, oil and protein in ratios of about 4:2:4 by weight. These particles were treated with formalin (37% formaldehyde), the desired rate being between 0.5 and 0.85% HCHO to protein in a sealed mixer and stored in a closed container for 8 days.

(B) Macrocyclic lactone 100 mg ivermectin (IVM) dissolved in 1 mL methylethyl ketone was mixed with 2 mL vegetable oil and then emulsified with 14% casein solution at pH 9. The emulsion was then freeze dried and comminuted to form finely dispersed particles containing IVM, oil and protein in ratios of about 1:20:20 by weight. These particles were treated with formaldehyde as described above in example 1(a).

EXAMPLE 2

Release of ABZ or IVM from a staged-release preparation

Samples each containing approximately 5 mg of ABZ or 0.15 mg IVM were incubated in vitro in rumen fluid at 39° C., and the ABZ or IVM content of the fluid was determined at fixed intervals thereafter. FIGS. 2 and 3 show that within 8 hours less than 10% of the staged-release ABZ or IVM preparation had become available. (The mean residence time of materials in the rumen is about 10 hours).

EXAMPLE 3

Availability in the abomasum of ABZ from a staged-release preparation

Samples similar to those described in Example 1(a) and (b) were incubated in vitro at 39° C. in freshly collected sheep abomasal fluid. Analyses of fluid samples are presented in FIGS. 2 and 3 and show that approximately 40% of ABZ and 15% of IVM is released from the respective staged release preparation within 2 hours (the normal residence time of materials in the abomasum is between 1 and 3 hours).

EXAMPLE 4

Relative availabilities of ABZ and IVM in the intestine

Sample ABZ and IVM preparations similar to those described in Example 1(a) and (b) were incubated in vitro at 39° C. in fresh fluid collected from the upper 3 m of the small intestine of sheep. From FIGS. 2 and 3 it will be seen that there is rapid release of solubilised ABZ and IVM from the staged-release form. The higher concentration of solubilised ABZ and IVM is probably due to the oil component of the particles increasing the partitioning of the ABZ and IVM into digesta fluid.

EXAMPLE 5

Comparison of rumen absorption in vivo

Figure 4:
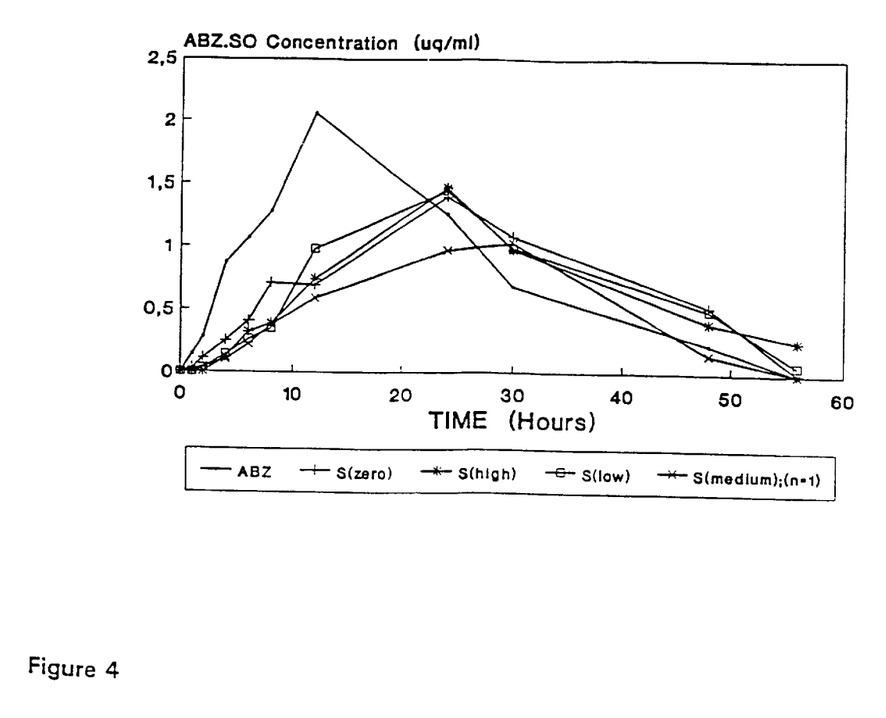
FIG. 4 shows the albendazole sulfoxide (ABZ.SO) plasma profiles of sheep into which ABZ had been intra-ruminally (IR) injected at a common dose rate of 3.9 mg ABZ/kg bodyweight.

FIG. 4 shows the ABZ.SO plasma profiles of sheep into which ABZ had been intra-ruminally (IR) injected at a common dose rate of 3.9 mg ABZ/kg bodyweight in preparations similar to those described in Example 1(a). For comparison, ABZ was also administered at 3.9 mg/kg as the commercial preparation "Valbazen".

Figure 5:
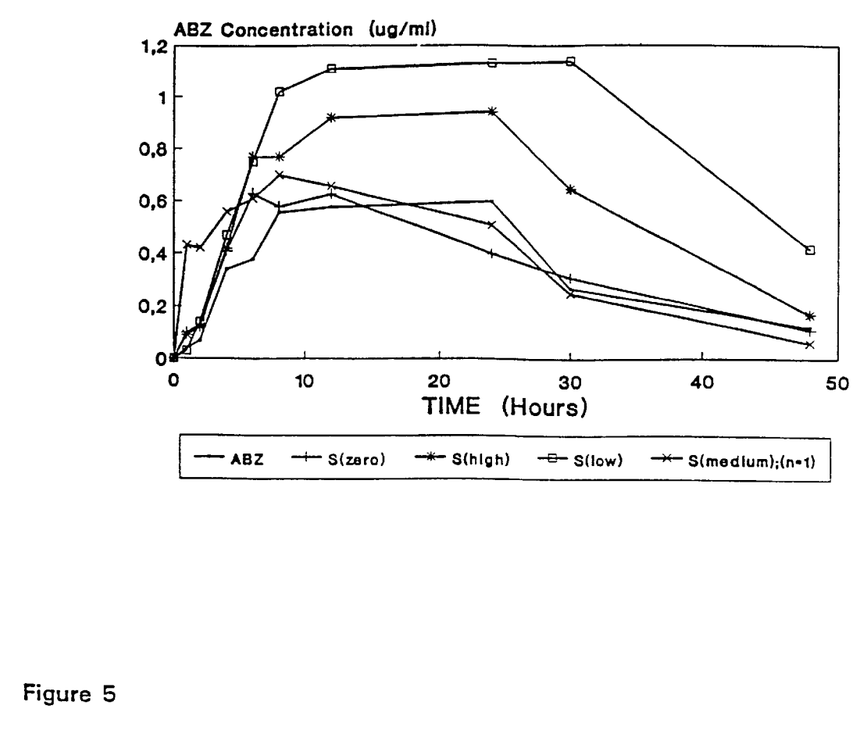
FIG. 5 shows the abomasal fluid profiles for ABZ which were determined during the trial described in Example 5.

The potential benefits of the rapid absorption of ABZ from the conventional preparation are not fully realised because much of the drug is excreted in the urine, whereas the slower uptake of ABZ from the staged-release preparation is more than compensated for by its release and higher availability in the abomasum and small intestine. Once the staged-release preparation has passed from the rumen and begins to degrade in the abomasum and small intestine, the dispersal of its ABZ component into the plasma, body tissues and the like then follows a similar time profile as that for ABZ administered in the conventional form. The abomasal fluid profiles for ABZ which were determined during the trial described in Example 5 are shown in FIG. 5. These clearly show the greater availability of ABZ from the staged-release preparation. Again, once degradation of the particles is complete (after 24–30 h), the elimination of ABZ from staged-release and conventional preparations occurs at a similar rate.

EXAMPLE 6

Absorption of staged-release ABZ after entry into the small intestine

Figure 6:
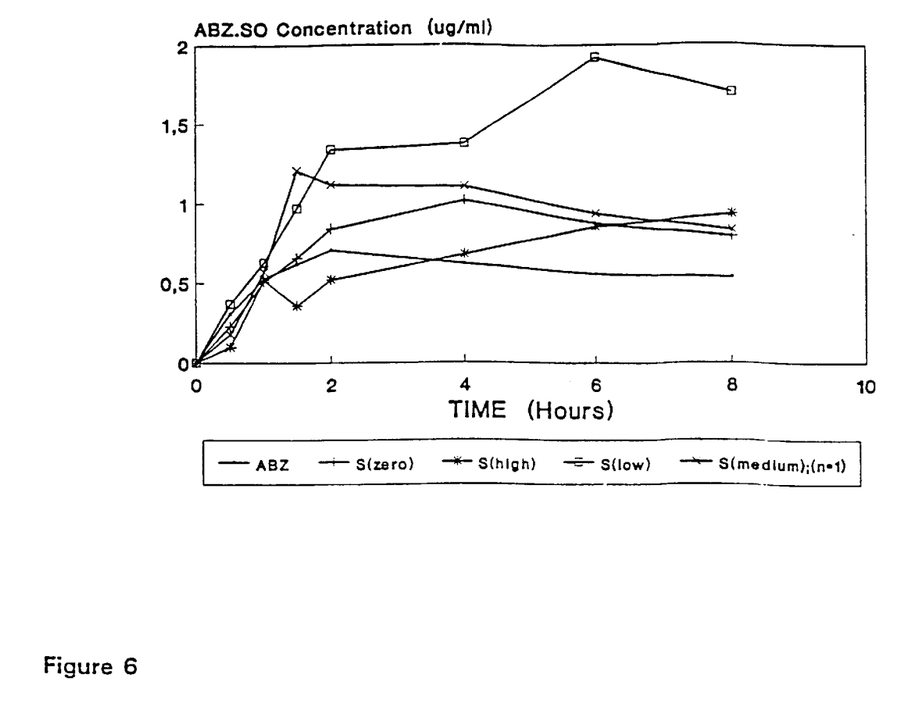
FIG. 6 shows the ABZ.SO plasma profiles after intra abomasal administration.

Samples similar to those described in Example 5 were administered by cannula directly into the abomasum (where virtually no absorption of ABZ takes place, but where the acidity of the environment brings about further degradation of the protective medium before it passes to the small intestine). Plasma samples were taken regularly thereafter and analysed for ABZ and its metabolites. The results are depicted in FIG. 6, and show that there is a greater absorption of ABZ from the staged-release preparation; this is believed to be due to the solubilising affect of the lipid component of the protective medium.

EXAMPLE 7

Anti-parasitic agent efficacies of the staged-release preparation and a conventional oral preparation Sheep were dosed intra-ruminally (at the rate of 3.9 mg/kg bodyweight) with "Valbazen" or with a preparation as described in Example 1. Total worm counts were carried out on test animals slaughtered after 10 days. The results are shown in the following table:

| | H. contortus | | T. colubriformis | |
|---|---|---|---|---|
| Treatment | Count | Efficacy (%) | Count | Efficacy (%) |
| Control | 3088 | 0 | 5699 | 0 |
| Valbazen | 667 | 78 | 2122 | 62 |
| S/R | 358 | 88 | 633 | 89 |

S/R = Staged-release preparation of ABZ
"Valbazen" (a registered trade mark) is an ABZ containing drench formulated by SmithKline Beecham Animal Health.

EXAMPLE 8

Comparison of absorption of IVM from the rumen

Figure 7:
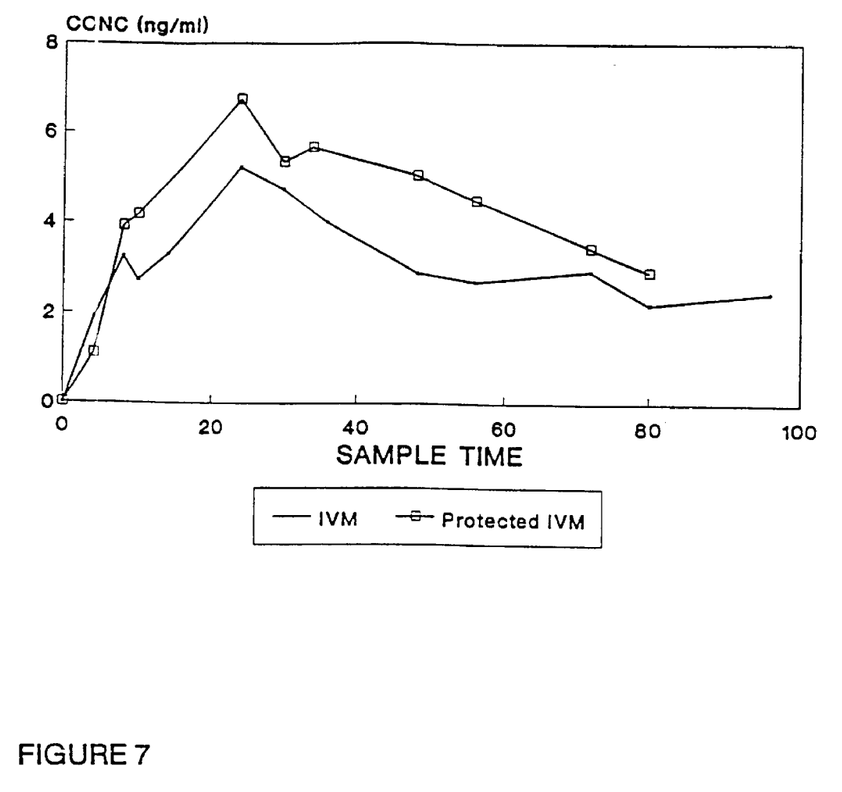
FIG. 7 shows the concentration of ivermectin in plasma after IR administration at a common dose of 200 µg/kg.

FIG. 7 shows the IVM profile of sheep which had been intra-ruminally injected with IVM at the rate of 0.2 mg/kg either as the commercial product "Ivomec" or as a protected IVM formulation similar to that described in Example 1(b).

The absorption of commercial IVM is limited since much of the dose strongly associates with digesta material or is degraded in the rumen, thus limiting availability for absorption from the abomasum and intestine. The benefit of protected IVM is that a greater proportion of the dose is presented to the abomasum and intestine in the form which is available for absorption. This is absorption produces a protracted profile of higher concentrations.

Initial appearance of IVM in the abomasal fluid did not differ between the two formulations since much of the drug which enters the abomasum quickly associates with digesta material. That is not to say that a greater quantity of IVM, following administration of the protected formulation, would not be released in the abomasum as described in relation to in vitro investigations (FIG. 3). Although IVM released in vivo would quickly pass from the fluid to particulate digesta its increased presence is not readily determined due to the difficulty of separating the IVM released from formulation particles, but associated with fine digesta material, from IVM remaining in the formulated particles. Accordingly, the HPLC assay for IVM in the abomasum was restricted to fluid only, but it is reasonable to expect that the behavior of the IVM in fluid would reflect overall availability in abomasumal digesta.

Figure 8:
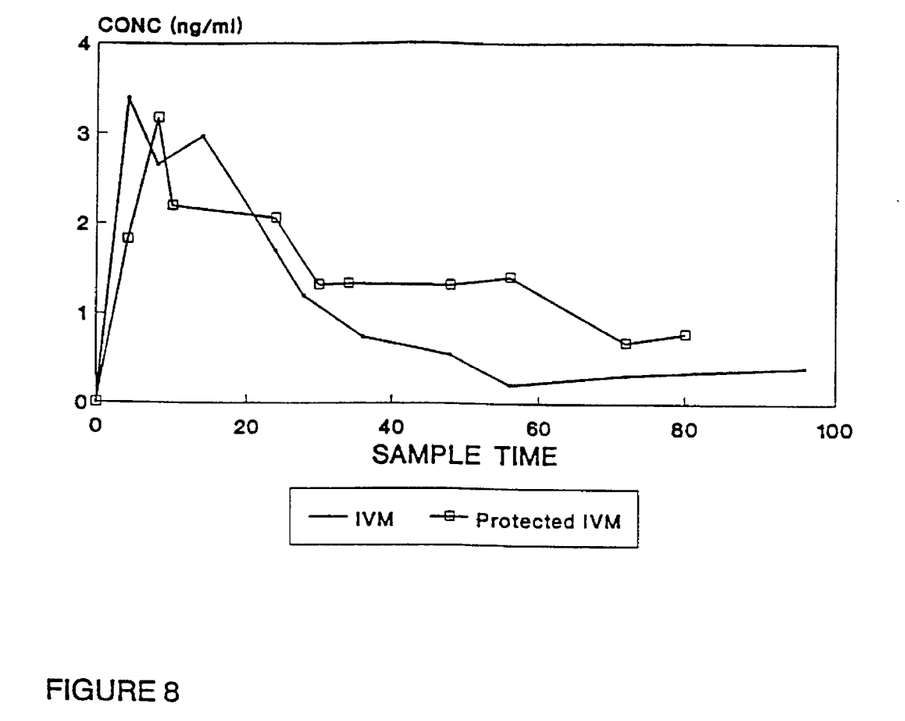
FIG. 8 shows the concentration of ivermectin in abomasal fluid after IR administration at a common dose of 200 µg/kg.

The greatly prolonged availability of IVM, as shown in plasma (FIG. 7) reflected an increased presence of IVM in abomasal fluid at concentrations greater than those following administration of the commercial preparation (FIG. 8).

EXAMPLE 9

Comparison of the availability of ABZ after administration to cattle

Figure 9:
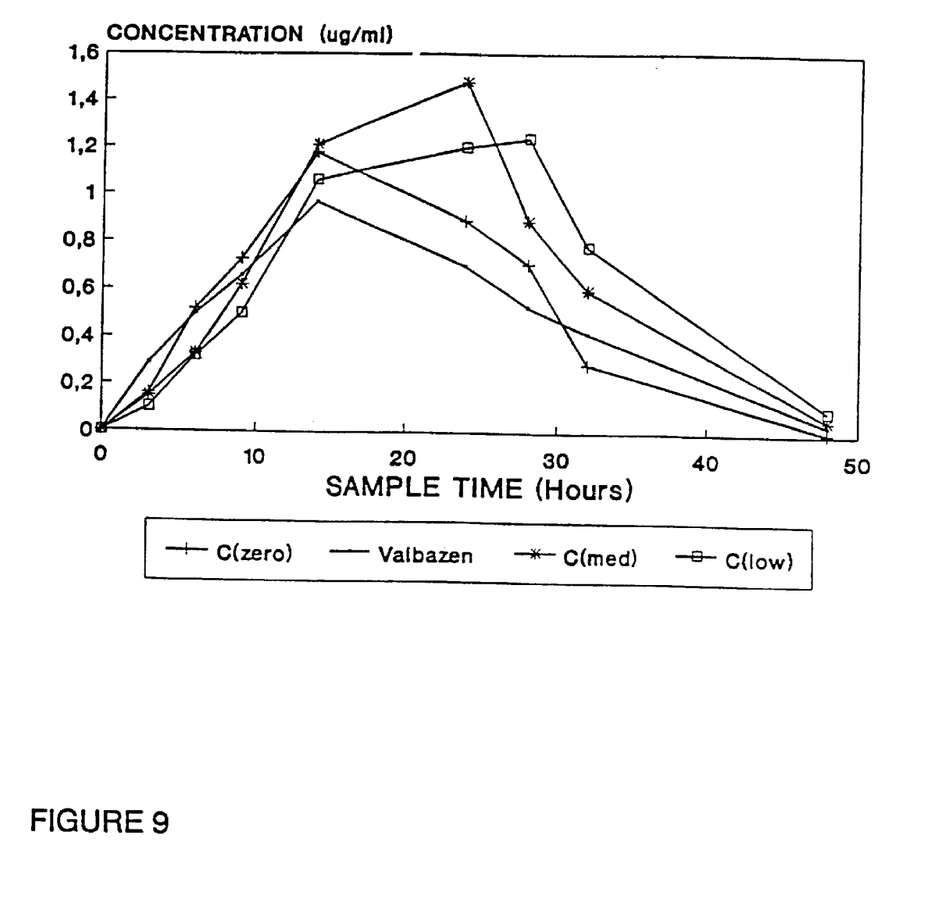
FIG. 9 shows the concentration-with-time profiles of ABZ.SO in plasma of cattle after IR administration of ABZ at a common dose rate of 7.5 mg/kg.

FIG. 9 shows the ABZ.SO plasma profiles of cattle into which ABZ had been intra-ruminally injected as the commercial preparation "Valbazen", or as protected formulations as described in Example 1(a), at a common dose rate of 7.5 mg ABZ/kg bodyweight. The concentrations of ABZ.SO increased similarly following administration of each formulation to 13 hours, but unlike the commercial product, ABZ.SO deriving from degradation of the protected formulations continued to rise to a maximum about 24 hours after administration, resulting in a much broader concentration-time profile.

Figure 10:
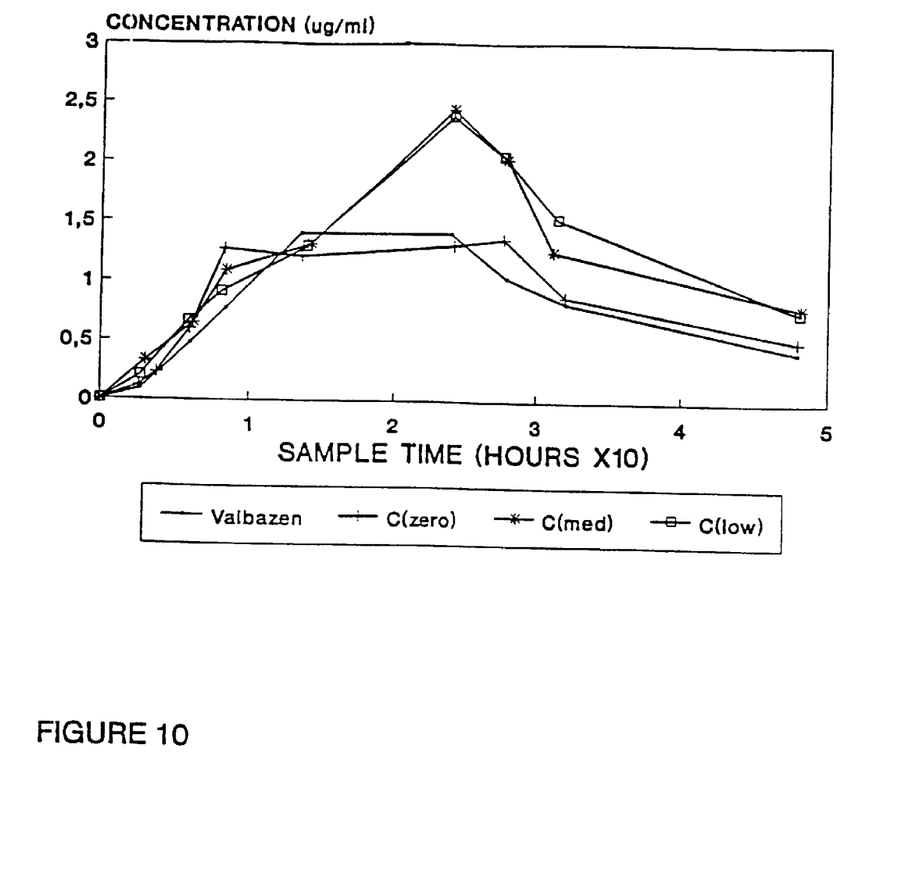
FIG. 10 shows the concentration-with-time profiles of ABZ in abomasal fluid of cattle after IR administration of ABZ at a common dose rate of 7.5 mg/kg.
Figure 11:
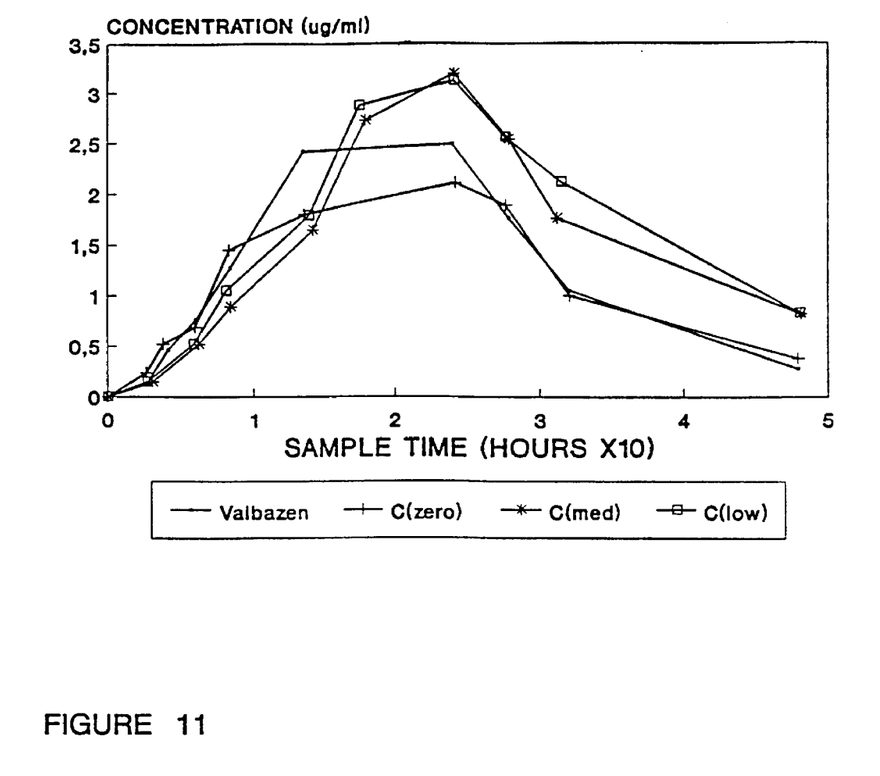
FIG. 11 shows the concentration-with-time profiles of ABZ.SO in abomasal fluid of cattle after IR administration of ABZ at a common dose rate of 7.5 mg/kg.

In the abomasum, the quantity of ABZ and ABZ.SO in digesta fluid was greatly enhanced with the protected formulation increasing the concentration and duration of drug availability (FIGS. 10 and 11).

In the foregoing examples the references to the ABZ content of rumen and other intestinal fluids are references to the solubilised ABZ content of fluids from which solids had been spun out, and which were determined using the high performance liquid chromatography procedures described by Hennessy et al 198[4].

INDUSTRIAL APPLICABILITY

The compositions and methods of the invention find use in animal health applications and simplify the administration of anti-parasitic agents to ruminants.

REFERENCES

1 Australian Patent 402712

2 Australian Patent 450530

3 Hennessy et al at the Joint Conference of the New Zealand and Australian Societies for Parasitology, Auckland 1992

4 Hennessy et al 1989, (*Journal of Veterinary Pharmacology and Therapeutics*, 12, 421–429).

We claim:

1. A particulate composition for combating and preventing parasite infestation of ruminants, which composition comprises an anti-parasitic agent selected from the group consisting of benzimidazoles, macrocyclic lactones, organophosphates, salicylanilides, substituted phenols, tetramisoles and pyrimidines dispersed in a dispersant comprising protein that is sufficiently cross-linked to cause said dispersant to have solubility characteristics offering sufficient degrees of resistance to the various environments encountered in a ruminant gastrointestinal tract, such that said agent is made available to said parasite in a non-zero amount from all of the rumen, the abomasum and the intestine, either directly or by absorption into the ruminant blood plasma, wherein, following oral administration, staged degradation of said dispersant causes effective, non-zero, amounts of the anti-parasitic agent to become available to the parasite by release during passage of the composition through each of the rumen, the abomasum and the intestine.

2. The composition of 1 wherein the antiparasitic agent is a benzimidazole.

3. The composition of claim 1, wherein the benzimidazole is selected from the group consisting of thiabendazole, albendazole, albendazole, sulfoxide, albendazole oxide, cambendazole, fenbendazole, mebendazole, oxfendazole, oxibendazole, parbendazole, cyclobendazole, flubendazole, triclabendazole and luxabendazole.

4. The composition of claim 1, wherein the antiparasitic agent is a macrocyclic lactone.

5. The composition of claim 1, wherein the macrocyclic lactone antiparasitic agent is an avermectin or milbemycin.

6. The composition of claim 5, wherein the avermectin or milbemycin is abamectin, ivermectin, doramectin or moxidectin.

7. The composition of claim 1, wherein the modified protein is based on plant or animal meals, casein or gelatin.

8. The composition of claim 1, wherein the cross-linking is effected by means of an aldehyde, tannin or polyvalent cation.

9. The composition of claim 1, wherein cross-linking is effected by heating.

10. The composition of claim 1 wherein the degree of cross-linking has been selected by reference to FIGS. 1, 2 or 3.

11. The composition of claim 1, wherein the dispersant is a lipid/protein matrix which has been cross-linked by treatment with an aldehyde.

12. A composition for combating and preventing parasite infestation of ruminants which comprises an anti-parasitic agent selected from the group consisting of benzimidazoles, macrocyclic lactones, organophosphates, salicylanilides, substituted phenols, tetramisoles and pyrimidines dispersed in a proteinaceous matrix that comprises a protein that is sufficiently modified to undergo staged degradation in each of the rumen, abomasum and intestine whereby causing non-zero quanitities of the anti-parasitic agent to be released in each of the rumen, abomasum and intestine.

13. A method for combating and preventing parasite infestation of a ruminant, which method comprises:

dispersing an anti-parasitic agent selected from the group consisting of benzimidazoles, macrocyclic lactones, organophosphates, salicylanilides, substituted phenols, tetramisoles and pyrimidines in a dispersant comprising a protein that is sufficiently cross-linked to possess solubility characteristics offering resistance to the various environments encountered in the ruminant gastrointestinal tract;

orally administering said dispersion to the ruminant, whereby causing said dispersion to pass through the rumen, the abomasum and the intestine of the ruminant;

following said oral administration, degrading said cross-linked dispersant while said dispersion is passing through each of the rumen, the abomasum and the intestine of the ruminant; and thereby causing effective non-zero amounts of the agent to become available to the parasite, either directly or by absorption into the ruminant's blood plasma, by release during passage of the degrading dispersion through each of the rumen, the abomasum and the intestine of the ruminant.

14. The method of claim 13 wherein the antiparasitic agent is a benzimidazole.

15. The method of claim 13, wherein the benzimidazole is selected from the group consisting of thiabendazole, albendazole, albendazole sulfoxide or albendazole oxide, cambendazole, fenbendazole, mebendazole, oxfendazole, oxibendazole, parbendazole, cyclobendazole, flubendazole, triclabendazole and luxabendazole.

16. The method of claim 13 wherein the antiparasitic agent is a macrocyclic lactone.

17. The method of claim 13, wherein the macrocyclic lactone antiparasitic agent is an avermectine or milbermycin.

18. The method of claim 17, wherein the avermectine or milbermycin is abamectine, ivermectin, doramectin or moxidectin.

19. The method of claim 13, wherein the protein is based on plant or animal meals, casein or gelatin.

20. The method of claim 13, wherein the cross-linking is effected by means of an aldehyde, tannin or polyvalent cation.

21. The method of claim 13, wherein cross-linking is effected by heating.

22. The method of claim 13 wherein the degree of cross-linking has been selected by reference to FIGS. 1 and 2 or 3.

23. The method of claim 13, wherein the dispersant comprises a lipid/protein matrix that has been cross-linked by treatment with an aldehyde.

24. In the method for combating and preventing parasite infestation of a ruminant, which method comprises oral administration to the ruminant of an anti-parasitic agent selected from the group consisting of benzimidazoles, macrocyclic lactones, organophosphates, salicylanilides, substituted phenols, tetramisoles and pyrimidines;

the improvement which comprises: administering said agent dispersed in a proteinaceous matrix that has been sufficiently cross-linked to permit it to undergo staged degradation during its passage through the rumen, abomasum and intestine of the ruminant whereby causing controlled release of non-zero amounts of the agent in each of the rumen, abomasum and intestine of the ruminant.

\* \* \* \* \*

UNITED STATES PATENT AND TRADEMARK OFFICE
CERTIFICATE OF CORRECTION

PATENT NO.    : 5,840,324
DATED         : November 24, 1998
INVENTOR(S)   : Hennessy et al.

It is certified that error appears in the above-identified patent and that said Letters Patent is hereby corrected as shown below:

<u>Title page,</u>
Kindly add the information on the Assignee to read:

-- Commonwealth Scientific and Industrial Organisation, Parkville, Australia and Meat Research Corporation, Sydney, Australia. --

Signed and Sealed this

Sixteenth Day of July, 2002

*Attest:*

JAMES E. ROGAN
*Attesting Officer*     *Director of the United States Patent and Trademark Office*